(12) United States Patent
Lambert et al.

(10) Patent No.: US 8,753,404 B2
(45) Date of Patent: Jun. 17, 2014

(54) HIP PROSTHESES

(75) Inventors: Richard Lambert, Germantown, TN (US); Terry McLean, Cordova, TN (US); David Kelman, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 762 days.

(21) Appl. No.: 11/233,911

(22) Filed: Sep. 23, 2005

(65) Prior Publication Data

US 2006/0217814 A1 Sep. 28, 2006

Related U.S. Application Data

(63) Continuation-in-part of application No. 10/243,502, filed on Sep. 13, 2002, now Pat. No. 6,986,792.

(51) Int. Cl.
*A61F 2/32* (2006.01)
*A61F 2/34* (2006.01)

(52) U.S. Cl.
CPC ........... *A61F 2/34* (2013.01); *A61F 2002/3241* (2013.01); *A61F 2002/3283* (2013.01); *A61F 2002/3291* (2013.01); *A61F 2002/3208* (2013.01); *A61F 2002/3233* (2013.01)
USPC ...................... 623/22.29; 623/22.2

(58) Field of Classification Search
CPC ............... A61F 2002/3241; A61F 2002/3258; A61F 2002/3266; A61F 2002/3283; A61F 2002/3291
USPC ............ 623/22.17–22.2, 22.24, 22.28, 22.29
See application file for complete search history.

(56) References Cited

U.S. PATENT DOCUMENTS

| | | | |
|---|---|---|---|
| 3,787,128 A | | 1/1974 | Maistrelli |
| 3,813,699 A | | 6/1974 | Giliberty |
| 3,818,512 A | * | 6/1974 | Shersher .................... 623/22.15 |
| 3,862,807 A | | 1/1975 | Doden et al. |
| 3,863,273 A | | 2/1975 | Averill |
| 3,874,003 A | | 4/1975 | Moser et al. |
| 3,875,593 A | * | 4/1975 | Shersher .................... 623/22.32 |

(Continued)

FOREIGN PATENT DOCUMENTS

| | | |
|---|---|---|
| EP | 0412438 A2 | 2/1991 |
| EP | 0 707 838 A | 4/1996 |
| EP | 0 945 109 A | 9/1999 |
| FR | EP 2765100 | 12/1998 |

OTHER PUBLICATIONS

Article entitled DUOLOX®—System aus Biolox® forte, *CeraNews*, 1 page (Feb. 1998).

(Continued)

*Primary Examiner* — Thomas J Sweet
*Assistant Examiner* — Cheryl Miller
(74) *Attorney, Agent, or Firm* — Ropes & Gray LLP

(57) ABSTRACT

Bipolar prostheses which include various structures and other techniques for optimizing material wear and mechanical strength properties. Such prostheses feature, for example, improved resistance to polyethylene wear while also reducing potential for dislocation of the femoral stem from the prosthesis. Such techniques and structures include varying wear resistance and mechanical strength treatment in various components of the prostheses or portions of those components as desired to improve, accentuate or optimize wear performance and dislocation reduction, locking ring structural features, structures for retaining locking rings in the bipolar prosthesis shell, and structures for limiting or reducing movement or rotation of locking rings and liners in bipolar prosthesis shells.

25 Claims, 5 Drawing Sheets

(56) References Cited

U.S. PATENT DOCUMENTS

| | | | |
|---|---|---|---|
| 3,882,550 A | 5/1975 | Karpf et al. | |
| 3,894,297 A | 7/1975 | Mitelmeier | |
| 4,044,403 A | 8/1977 | D'Errico | |
| 4,141,088 A | 2/1979 | Treace et al. | |
| 4,172,296 A | 10/1979 | D'Errico | |
| 4,241,463 A | 12/1980 | Khovaylo | |
| 4,380,090 A * | 4/1983 | Ramos | 623/22.2 |
| 4,408,360 A * | 10/1983 | Keller | 623/22.2 |
| 4,437,193 A | 3/1984 | Oh | |
| 4,473,068 A | 9/1984 | Oh | |
| 4,475,549 A | 10/1984 | Oh | |
| 4,619,658 A | 10/1986 | Pappas et al. | |
| 4,623,352 A | 11/1986 | Oh | |
| 4,624,674 A | 11/1986 | Pappas et al. | |
| 4,632,111 A | 12/1986 | Roche | |
| 4,642,123 A | 2/1987 | Noiles | |
| 4,673,409 A | 6/1987 | Van Kampen | |
| 4,676,798 A | 6/1987 | Noiles | |
| 4,676,799 A | 6/1987 | Legrand | |
| 4,678,472 A | 7/1987 | Noiles | |
| 4,695,282 A | 9/1987 | Forte et al. | |
| 4,718,908 A | 1/1988 | Wigginton et al. | |
| 4,718,911 A | 1/1988 | Kenna | |
| 4,729,041 A | 3/1988 | Kuroda | |
| 4,770,658 A | 9/1988 | Geremakis | |
| 4,784,663 A | 11/1988 | Kenna | |
| 4,795,469 A | 1/1989 | Oh | |
| 4,795,471 A * | 1/1989 | Oh | 623/22.19 |
| 4,798,610 A | 1/1989 | Averill et al. | |
| 4,883,490 A | 11/1989 | Oh | |
| 4,919,674 A * | 4/1990 | Schelhas | 623/22.29 |
| 4,936,855 A | 6/1990 | Sherman | |
| 4,950,299 A | 8/1990 | Noiles | |
| 4,960,427 A | 10/1990 | Noiles | |
| 4,990,149 A | 2/1991 | Fallin | |
| 4,995,883 A | 2/1991 | Demane et al. | |
| 4,997,447 A | 3/1991 | Shelley | |
| 5,019,105 A | 5/1991 | Wiley | |
| 5,037,438 A * | 8/1991 | Davidson | 623/22.15 |
| 5,047,033 A | 9/1991 | Fallin | |
| 5,049,158 A | 9/1991 | Engelhardt et al. | |
| 5,062,853 A * | 11/1991 | Forte | 623/22.2 |
| 5,078,746 A | 1/1992 | Garner | |
| 5,080,677 A | 1/1992 | Shelley | |
| 5,092,898 A * | 3/1992 | Bekki et al. | 623/22.16 |
| 5,108,452 A | 4/1992 | Fallin | |
| 5,133,763 A | 7/1992 | Mullers | |
| 5,156,626 A | 10/1992 | Broderick et al. | |
| 5,181,926 A | 1/1993 | Koch et al. | |
| 5,193,679 A | 3/1993 | White | |
| 5,217,499 A | 6/1993 | Shelley | |
| 5,222,984 A * | 6/1993 | Forte | 623/22.18 |
| 5,226,917 A | 7/1993 | Schryver | |
| 5,263,988 A | 11/1993 | Huebner | |
| 5,310,408 A | 5/1994 | Schryver et al. | |
| 5,314,487 A | 5/1994 | Schryver et al. | |
| 5,314,491 A | 5/1994 | Thongpreda et al. | |
| 5,324,291 A | 6/1994 | Ries et al. | |
| 5,350,381 A | 9/1994 | Melton | |
| 5,358,532 A | 10/1994 | Evans et al. | |
| 5,383,938 A | 1/1995 | Rohr et al. | |
| 5,405,005 A | 4/1995 | White | |
| 5,405,392 A | 4/1995 | Deckner | |
| 5,425,778 A | 6/1995 | Zichner et al. | |
| 5,425,779 A * | 6/1995 | Schlosser et al. | 623/22.2 |
| 5,456,717 A | 10/1995 | Zweymuller et al. | |
| 5,507,826 A * | 4/1996 | Besselink et al. | 623/22.29 |
| 5,507,830 A | 4/1996 | Demane et al. | |
| 5,549,681 A | 8/1996 | Segmuller et al. | |
| 5,549,702 A | 8/1996 | Ries et al. | |
| 5,571,105 A | 11/1996 | Gundolf | |
| 5,593,446 A | 1/1997 | Kuoni | |
| 5,676,704 A | 10/1997 | Ries et al. | |
| 5,725,587 A | 3/1998 | Garber | |
| 5,755,807 A * | 5/1998 | Anstaett et al. | 623/22.2 |
| 5,782,928 A | 7/1998 | Ries et al. | |
| 5,800,555 A | 9/1998 | Gray, III | |
| 5,824,108 A | 10/1998 | Huebner | |
| 5,879,404 A | 3/1999 | Bateman et al. | |
| 5,879,405 A | 3/1999 | Ries et al. | |
| 5,888,211 A | 3/1999 | Sanders | |
| 5,916,270 A | 6/1999 | Lipman | |
| 5,931,870 A | 8/1999 | Cuckler et al. | |
| 5,989,293 A * | 11/1999 | Cook et al. | 623/22.29 |
| 6,042,611 A | 3/2000 | Noiles | |
| 6,042,612 A | 3/2000 | Voydeville | |
| 6,059,833 A | 5/2000 | Doets | |
| 6,096,083 A * | 8/2000 | Keller et al. | 623/22.11 |
| 6,129,765 A | 10/2000 | Lopez et al. | |
| 6,136,037 A | 10/2000 | Hussig et al. | |
| 6,162,227 A | 12/2000 | Eckhardt et al. | |
| 6,165,220 A | 12/2000 | Shen et al. | |
| 6,206,929 B1 * | 3/2001 | Ochoa et al. | 623/22.17 |
| 6,248,132 B1 | 6/2001 | Hararis | |
| 6,270,502 B1 | 8/2001 | Stulberg | |
| 6,325,829 B1 | 12/2001 | Schmotzer | |
| 6,328,764 B1 * | 12/2001 | Mady | 623/22.16 |
| 6,334,875 B1 | 1/2002 | Keller | |
| 6,344,060 B1 | 2/2002 | Schmotzer et al. | |
| 6,365,089 B1 * | 4/2002 | Krebs et al. | 264/485 |
| 6,436,147 B1 | 8/2002 | Zweymuller | |
| 6,451,058 B2 | 9/2002 | Tuke et al. | |
| 6,494,917 B1 | 12/2002 | McKellop et al. | |
| 6,527,808 B1 | 3/2003 | Albertorio et al. | |
| RE38,058 E | 4/2003 | Fallin | |
| 6,540,788 B1 | 4/2003 | Zweymuller | |
| 6,613,094 B2 | 9/2003 | Zweymuller | |
| 6,626,913 B1 | 9/2003 | McKinnon | |
| 6,652,289 B2 | 11/2003 | Bae | |
| 6,746,452 B2 | 6/2004 | Tuke et al. | |
| 6,808,539 B2 | 10/2004 | Zweymuller | |
| 6,916,342 B2 | 7/2005 | Frederick et al. | |
| 6,966,932 B1 * | 11/2005 | Schroeder | 623/22.19 |
| 6,986,792 B2 * | 1/2006 | McLean et al. | 623/22.29 |
| 7,004,973 B2 | 2/2006 | Zweymuller | |
| 7,074,241 B2 | 7/2006 | McKinnon | |
| 7,160,307 B2 | 1/2007 | Harwood et al. | |
| 7,160,332 B2 | 1/2007 | Frederick et al. | |
| 7,175,668 B2 | 2/2007 | Zweymuller | |
| 7,179,297 B2 | 2/2007 | McLean | |
| 7,250,054 B2 | 7/2007 | Allen et al. | |
| 7,255,701 B2 | 8/2007 | Allen et al. | |
| 7,335,231 B2 | 2/2008 | McLean | |
| 7,374,576 B1 | 5/2008 | Ries et al. | |
| 7,455,693 B2 | 11/2008 | Zweymuller | |
| 7,494,510 B2 | 2/2009 | Zweymuller | |
| 7,497,875 B1 | 3/2009 | Zweymuller | |
| 7,534,271 B2 | 5/2009 | Ries et al. | |
| 7,575,603 B2 | 8/2009 | Bergin et al. | |
| 7,591,821 B2 | 9/2009 | Kelman | |
| 7,621,915 B2 | 11/2009 | Frederick et al. | |
| 7,682,398 B2 | 3/2010 | Croxton et al. | |
| 7,749,277 B2 | 7/2010 | McLean | |
| 7,749,278 B2 | 7/2010 | Frederick et al. | |
| 7,780,667 B2 | 8/2010 | Watanabe et al. | |
| 7,828,806 B2 | 11/2010 | Graf et al. | |
| 7,863,410 B2 | 1/2011 | Smith et al. | |
| 7,879,106 B2 | 2/2011 | McMinn | |
| 7,892,290 B2 | 2/2011 | Bergin et al. | |
| 7,901,411 B2 | 3/2011 | Frederick et al. | |
| 2003/0050703 A1 | 3/2003 | Harris et al. | |
| 2004/0054418 A1 | 3/2004 | McLean | |
| 2004/0143341 A1 | 7/2004 | McLean | |
| 2004/0225369 A1 | 11/2004 | Lakin et al. | |
| 2005/0102033 A1 * | 5/2005 | Lambert et al. | 623/22.21 |
| 2008/0015707 A1 | 1/2008 | Lambert et al. | |

OTHER PUBLICATIONS

Smith & Nephew—Orthopaedics—Convene Bipolar System http://ortho.smith-nephew.com/us/Standard.asp?NodeId=219, 1 page (Aug. 2, 2002).

Smith & Nephew—Orthopaedics—Convene® Bipolar System Surgical Techniquehttp://ortho.smith-nephew.com/us/Flash.asp?NodeId=3155, 7pages (Aug. 2, 2002).

(56) References Cited

OTHER PUBLICATIONS

Wheeless' Textbook of Orthopaedics—Bipolar Arthroplasty http://www.medmedia.com/o14/51.htm, 2 pages (Aug. 2, 2002).
Joint Replacement—Hip Systems—Hip Heads—Mathys Join Replacement http://www.mathysmedical.ch/products/ortho/hip/heads/ortho_hip_heads_cem.html, 2 pages (Aug. 2, 2002).
Plus Orthopaedics—Design Rationale—Bipolar http:/www.plusortho.com/dr_bipolar.html, 3 pages (Aug. 2, 2002).
Smith & Nephew Brochure Entitled Reflection[†] XLPE Cross-linked Polyethylene Acetabular Liners, 16 pages (Apr. 2002).
Office Action dated Jun. 20, 2008 in related U.S. Appl. No. 11/828,656.
Response dated Oct. 17, 2008 in related U.S. Appl. No. 11/828,656.
Interview Summary dated Oct. 23, 2008 in related U.S. Appl. No. 11/828,656.
Office Action dated Jan. 2, 2009 in related U.S. Appl. No. 11/828,656.
Response dated Apr. 2, 2009 in related U.S. Appl. No. 11/828,656.

* cited by examiner

HIP PROSTHESES

This application is a continuation-in-part of U.S. patent application Ser. No. 10/243,502, now U.S. Pat. No. 6,986,792, filed Sep. 13, 2002, the entire contents of which are hereby incorporated by reference. This invention relates to improved prostheses, including bipolar prostheses, suited to reduce polyethylene wear and potential of femoral/acetabular dislocation.

BACKGROUND

Bipolar prostheses generally provide two bearing surfaces between the (artificial) femoral head and the acetabulum. The first bearing surface is the typically smooth outer surface of the bipolar prosthesis shell, which may be formed of metal, ceramic material or as otherwise desired. A liner, conventionally formed of polyethylene material such as ultra high molecular weight polyethylene, may be adapted to fit tightly within the shell and provide an inner bearing surface which receives and cooperates with the femoral head in an articulating relationship to track and accommodate the relative movement between the femur and the acetabulum.

This dual bearing surface design is often indicated for patients whose acetabulae are relatively healthy and able to accommodate a prosthetic proxy for the anatomical femoral head. Bipolar prostheses leverage the theory that erosion and protrusion of the acetabulum will be less where articulating motion is absorbed by two bearing surfaces rather than one, i.e., relative movement between the shell outer surface and the acetabulum on the one hand and between the femoral stem head and the prosthesis liner on the other. The dual bearing surface thus distributes shear forces between the inner and outer bearings in order to spare the acetabular surface from wear and erosion. Additionally, acetabular wear is diminished through reduction of relative motion between the acetabular anatomy and the outer surface of the prosthesis because the inner bearing formed by the liner against the femoral stem head also absorbs some of the motion. Moreover, the dual bearing surfaces typically provide greater range of motion than provided by either unipolar designs or conventional total hip arthoroplasty.

Even though bipolar prostheses are well beyond the first generation of design and implementation, a number of issues remain. These include (1) the potential for dislocation of the femoral stem head relative to the shell/liner; and (2) polyethylene wear issues. (These two issues, as discussed more fully below, arise not only in the context of bipolar prostheses, but also in the context of acetabular components used in total hip replacement surgery and other joint prostheses.)

The dislocation problem is exacerbated because dislocations often require surgical intervention to reestablish the prosthetic/hip joint. Accordingly, conventional bipolar designs and other hip prosthesis designs, often feature a snug fit in which the stem head is captured in the liner. Such designs include a reduced diameter liner opening through which the stem head is forced before installation of the shell/liner. Other designs feature retention rings or locking rings. However, overemphasis on dislocation prevention can reduce range of motion between the femoral stem and the shell/liner. Additionally, previous designs are limited by the extent to which the polyethylene can "stretch" to accommodate the stem head in a capture fit. That extent may be insufficient for optimal dislocation prevention in non-locking ring designs. Some previous locking ring designs in bipolar prostheses have accommodated the issue by including a split in the annulus formed by the locking ring so that the diameter of the locking ring may be expanded for penetration of the stem head before installation of the prosthesis, and contracted again for installation in a manner that seeks to effectively capture the stem head and thus prevent dislocation. Split rings, however, present their own sets of issues, including potential to expand and contract in diameter even after installed which can in turn introduce polyethylene wear issues in addition to unacceptable "pistoning" of the stem head in the liner with potential polyethylene wear and stability complications.

Polyethylene wear has been recognized as an undesirable effect sometimes caused by articulating and non-articulating relative motion between a polyethylene surface and another surface such as, for instance, a metal surface such as that of a bearing in a hip prosthesis. One reason that polyethylene wear is considered serious is that even a very small volume of polyethylene debris actually includes a great number of polyethylene particles. For instance, one cubic millimeter of polyethylene wear debris can include up to ten trillion polyethylene particles. These particles are believed to cause osteolysis when they escape into nearby bone and tissue. Such polyethylene wear can occur between surfaces which articulate relative to one another and surfaces which are intended not to articulate but only engage only in so-called "micromotion."

Various approaches have been adopted in recent times in order to reduce generation of polyethylene wear debris. These include careful and specialized treatment of the polyethylene and the metal or other surfaces which bear against the polyethylene. They also include measures to enhance wear performance of the polyethylene such as irradiation and other processes employed to increase cross-linking or other material properties in the polyethylene. While cross-linking is advantageous to enhance polyethylene wear performance, it can also reduce mechanical and physical properties of the polyethylene such as, for instance, yield strength, tensile strength, elongation and impact strength. Accordingly, while cross-linking measures are useful for reducing wear of polyethylene in bipolar prostheses, polyethylene liners and locking rings formed of cross-linked polyethylene can suffer reduced ability to capture and retain a femoral stem head in order to prevent dislocation.

SUMMARY OF THE INVENTION

Various embodiments of the present invention include various structures and techniques for reducing polyethylene wear while at the same time increasing or at least not compromising ability of the shell/liner (or simply a shell) in a hip prosthesis to reduce or prevent dislocation of the femoral stem head.

According to a first group of aspects according to certain embodiments of the invention, material properties of portions of the shell/liner, shell, and/or locking ring located at predetermined locations on those structures can be altered such as by treating the material at those locations, in order to emphasize wear performance, while other locations can be altered, treated differently, or not treated in order to emphasize other properties such as yield strength, tensile strength, elongation, and impact strength, among other properties. As a first example, in a total hip replacement acetabular component, portions of a polyethylene liner locked in a metallic shell could be treated to improve cross-linking at locations deep in the liner that are expected to absorb more compressive load from the femoral head, while portions which are located closer to the lip may omit such treatment so that they feature improved yield strength, tensile strength, elongation properties, impact strength, and other mechanical properties that tend to aid the liner in retaining the femoral head in the liner.

As a second example, in a bipolar prosthesis which includes a metallic shell with a polyethylene liner and a polyethylene retaining or locking ring, the liner may be formed of polyethylene which has been treated to improve cross linking or other properties that improve resistance to polyethylene wear, while the retaining or locking ring is not so treated, treated to a lesser extent, or otherwise treated, in order to optimize mechanical properties that help the locking ring retain the femoral head and thus prevent dislocation of the head from the bipolar prosthesis. As a third example, portions of the metallic shell and/or femoral stem head can be made or treated in order to improve wear performance against polyethylene surfaces, including formation or treatment to impart special finishes or compositions. Thus, bipolar prosthetic and other prosthetic components which feature polyethylene treatment of the sort mentioned above or other location and/or property-sensitive polyethylene treatment as disclosed herein, can be combined with shells and/or heads on which special surfaces such as an oxidized zirconium surface has been imparted.

According to certain aspects of certain embodiments of the invention, structures and processes according to certain embodiments of the present invention exploit optimum performance properties of various types of irradiated polyethylene materials. Because it has been generally recognized that cross-linked polyethylene which has been irradiated according to conventional and other techniques exhibits improved wear performance when placed in articulating and non-articulating relationships with metal and other surfaces, certain structures and processes according to certain embodiments of the present invention optimize cross linking of various regions of the liner which are in a position to accept increased load from the femoral stem head. These portions may include some or all of the liner, including carefully selected regions. On the other hand, the locking ring, or portions of it, may be formed of non or reduced cross-linked polyethylene in order to optimize properties such as yield strength, tensile strength, elongation and impact strength. The irradiation may occur according to any desired process, including irradiation of stock polyethylene material to whatever desired degree, irradiation of all or portion of components after they are formed into shape, combinations of these techniques, or as otherwise desired. Such optimized performance thus allows bipolar prostheses according to certain aspects of the present invention to minimize polyethylene wear while at the same time featuring acceptable or improved dislocation prevention properties. Accordingly, various embodiments of the invention relate to the use of cross-linked polyethylene (XLPE) in a bipolar hip implant. The XLPE may be used in combination with other types of polyethylene or any other suitable materials. In certain embodiments, a minimum of two different types of polyethylene or other materials are used, one of which preferably enhances the bearing performance and wear properties of the bipolar implant. In other words, two different types of polyethylene (as opposed to treating the surface of one type of polyethylene with varying crosslinking) may be used to provide a multi-material liner.

According to another group of aspects of certain embodiments of the present invention, various mechanical and physical structures for bipolar prostheses in particular assist in improving wear performance and resistance to dislocation.

As a first example of such mechanical or physical structures, certain bipolar prosthesis structures according to certain embodiments of the present invention feature non-split locking rings which are adapted to be placed over the neck of a two-piece femoral stem before the head is mounted on the stem. The non-split locking ring thus features a substantially smaller opening diameter than the largest diameter of the femoral stem head so that it more effectively captures the head and reduces potential of dislocation. These aspects of the invention accordingly take advantage of modular hip stem designs, which allows the ring to be assembled on the stem before the head is mounted, before the head and locking ring are then assembled into the shell or shell/liner, in order to create a tighter locking ring constriction.

Such non-split locking rings can be adapted to be introduced and retained in the shell/liner combination or the shell using any retention component or approach, including without limitation an interference fit, a reverse biased lip, retention ring which is captured in a shell and captures liner lip or outer surfaces, or an indentation or groove formed in the outer surface of the locking ring which corresponds to an indentation or groove formed on the inner surface of the shell. A metal retainer such as a circular ring formed of appropriate spring metal can form a component in these structures.

Additionally, the locking ring, whether split or non-split, may feature irregularities such as a peripheral tab, protrusion or indentation which corresponds with and cooperates with structure on the inner surface of the shell in order to reduce or prevent rotation of the locking ring within the shell. Such reduced rotation reduces wear of polyethylene or other material from which the locking ring is formed.

In various structures according to certain embodiments of the present invention, which include a polyethylene liner within the shell, the liner outer surface can also include an irregularity such as a ridge or an indentation which cooperates with corresponding structure on the inner surface of the shell. These surfaces can accordingly preclude or reduce rotation of the liner in a shell in order to reduce wear of the materials of which the shell and/or liner are formed.

It is accordingly an object of certain aspects of certain embodiments of the present invention to provide prostheses which enhance polyethylene wear performance properties while at the same time enhancing or not compromising ability of the prosthesis to prevent or reduce dislocation of the femoral stem.

It is an additional object of certain aspects of certain embodiments of the present invention to provide hip prosthesis in which portions of a bearing surface which cooperates with a femoral stem head accentuate, improve or optimize a first set of properties such as material wear performance, and other portions of the surface accentuate, improve or optimize a second set of properties such as yield strength, tensile strength, elongation properties, and/or impact strength.

It is an additional object of certain aspects of certain embodiments of the present invention relating to hip prostheses which feature a shell and a liner, to provide a liner in which portions improve, accentuate or optimize a first set of properties such as material wear performance, and other portions improve, accentuate or optimize a second set of properties such as yield strength, tensile strength, elongation properties, and/or impact strength. The liner may be a multi-material liner, e.g., formed from more than one type of material. In certain embodiments, the liner is formed from two different types of material, one of which is treated to enhance wear properties (e.g., cross-linked polyethylene and standard polyethylene). (For the purposes of this application, treated polyethylene and standard polyethylene are considered two different types of material, and a liner made of both types of material (or made of any other different types of materials) would be considered a multi-material liner.)

It is an additional object of certain aspects of certain embodiments of the present invention relating to hip prostheses which feature a shell, a liner and a locking ring, to provide a liner, and if desired a locking ring, in which portions improve, accentuate or optimize a first set of properties such as material wear performance, and other portions improve, accentuate or optimize a second set of properties such as yield strength, tensile strength, elongation properties, and/or impact strength.

It is an additional object of certain aspects of certain embodiments of the present invention relating to hip prostheses which feature a shell without liner, to provide a shell in which portions improve, accentuate or optimize a first set of properties such as material wear performance, and other portions improve, accentuate or optimize a second set of properties such as yield strength, tensile strength, elongation properties, and/or impact strength.

It is an additional object of certain aspects of certain embodiments of the present invention to provide bipolar hip prostheses which include a liner at least a portion of which is formed of polyethylene that enhances wear performance, and a locking ring at least a portion of which is formed of polyethylene which enhances mechanical performance properties such as yield strength, tensile strength, elongation and impact strength.

It is an additional object of certain aspects of certain embodiments of the present invention to provide bipolar prostheses with a locking ring that is designed to take advantage of two-piece femoral stem designs which permit the locking ring to be assembled onto the femoral stem before the head is mounted on the stem.

It is an additional object of certain aspects of certain embodiments of the present invention to provide bipolar prostheses which include mechanical structure to preclude or reduce relative motion between the locking ring and the shell and/or between the liner and the shell in order to reduce polyethylene wear.

It is an additional object of certain aspects of certain embodiments of the present invention to provide bipolar prostheses which employ a locking ring held in place by a retainer captured in a groove or cooperating with other structure in the outer surface of the locking ring in order to reduce relative motion between the locking ring and the shell and reduce pistoning and other undesired relative motion between the femoral stem head and the shell or liner.

Other objects, features, and advantages of the invention and certain aspects and embodiments of it will become apparent with respect to the remainder of this document.

DETAILED DESCRIPTION a. Particular Bipolar Prosthetic Structures for Improving Material Wear and Dislocation Properties.

Figure 1:
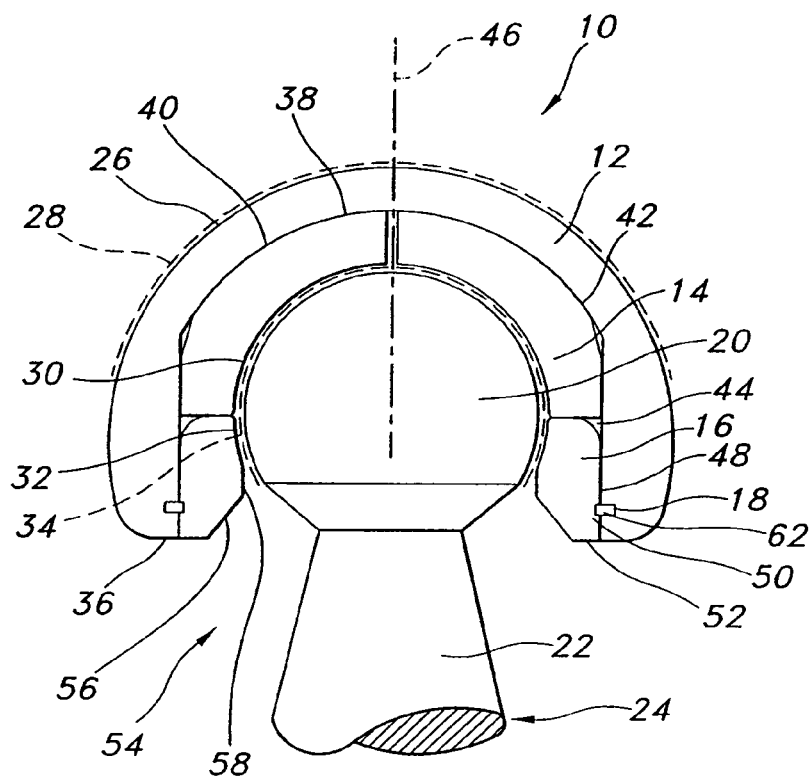
FIG. 1 shows a cross-sectional view of a preferred embodiment of a prosthesis according to certain aspects of the present invention.

FIG. 1 is a cross-sectional view showing a preferred embodiment of a bipolar prosthesis 10 according to certain aspects of the present invention. Prosthesis 10 generally includes a shell 12 which receives a liner 14 and a locking ring 16 which may be held in place by a retainer 18. The prosthesis 10 is adapted to fit within and articulate, or fit in an articulating relationship with, the acetabulum. "Articulating relationship" means a physical relationship that allows relative motion or movement between two components of a prosthesis in a manner that corresponds to motion or movement of two body parts relative to each other, such as bone structure on opposing sides of a joint such as an ankle, knee, hip, wrist, elbow or shoulder. For instance, prosthesis 10 and a femoral stem it accommodates are connected in an articulating relationship, while the liner fixed within the prosthesis may not be connected in an articulating relationship with the shell. The stem and the prosthesis "articulate" relative to each other.

Prosthesis 10 is adapted to receive head 20 which is mounted (such as using a Morse taper) on neck 22 of a femoral stem 24. Femoral stem 24 and these components may be any desired conventional stem components, formed of any desired materials.

Prosthesis 10 is thus adapted to be positioned in articulating relationship relative to a patient's acetabulum and relative to femoral stem 24. The outer surface 26 of shell 12 forms an outer bearing surface which cooperates with the acetabulum tissue to form an outer bearing 28. The inner, bearing surface 30 of liner 14 and the inner, bearing surface 32 of locking ring 16 cooperate with the femoral stem head 20 to form an inner bearing 34.

Shell 12 may be formed of any desirable material conventionally used for bipolar shells, including various metallic or ceramic materials. Outer surface 26 may be finished with a mirror surface, polished, or otherwise finished for optimum articulation relative to the acetabulum. Outer surface 26 may form a portion of a sphere, an ovaloid structure or shaped as otherwise desired in order to optimize articulation while at the same time reducing potential for migration and dislocation. It may be equal to or form more or less than half of such a structure; for instance, outer surface 26 may be hemispherical, more shallow than hemispherical or deeper than hemispherical as desired.

Outer surface 26 of shell 12 may round or otherwise transition to a portal surface 36 of shell 12. Portal surface 36 as well as the transition may assume any desired shape in order to accommodate the form, function and fit of prosthesis 10.

A shell cavity 38 is formed by a shell inner surface 40. As shown in FIG. 1, a first portion of shell cavity 38 may be dome shaped, hemispherical, or otherwise formed of a surface of rotation or as otherwise desired while a second portion, closer to portal surface 36, may be cylindrical or otherwise shaped as desired. Cavity 38 is formed to accept and receive liner 14 and locking ring 16. It may be shaped and surfaced as desired in order to optimize the preferably non-articulating relationship between shell 12 and liner 14 on the one hand and shell 12 and locking ring 16 on the other hand.

Liner 14, and ring 16, or desired portions of one or both of them, may be formed of various types of polyethylene in a continuous or discontinuous fashion to improve, accentuate or optimize properties such as wear performance. For instance, all of liner 14 may be formed of highly crosslinked high-density polyethylene which has been irradiated or otherwise treated, before or after being formed into the shape that corresponds to liner 14, while all of locking ring 16 may omit such treatment in order to retain mechanical properties that help resist femoral stem dislocation, such as yield strength, tensile strength, elongation properties, and/or impact strength. Any cross-linking or wear resistance treatment of the materials from which liner 14 or locking ring 16 are made can be employed. Treatment can also occur to enhance wear performance during or after the liner 14 and/or locking ring 16 have been formed into shape. A combination of these techniques can be employed.

Alternatively, various portions of liner 14 and/or ring 16, such as those on the liner near the axis of rotation 46, and/or locations on the locking ring 16 surface which bear against the head of a femoral stem in articulating relationship can, for instance, feature polyethylene or other materials which have been treated at desired levels to improve wear resistance. Treatment may be varied according to various locations in liner 14, such as cross linking treatment being reduced gradually across the continuum that extends from the axis of rotation 46 to the liner interface surface 44. According to such wear resistance treatment, properties of various locations of liner 14 may feature improved, accentuated or optimized wear resistance, and other locations can feature improved, accentuated, or optimized mechanical properties such as yield strength, tensile strength, elongation and impact strength.

Liner 14 as shown in FIGS. 1-5 is adapted and configured to be received, preferably snugly, in non-articulating relationship with cavity 38 and shell 12. Liner 14 accordingly, in the embodiment shown in FIGS. 1-5, features an outer surface 42 with a first portion corresponding to the first portion of cavity 38 and a second portion generally corresponding to the second portion of cavity 38. An irregularity 75 such as a groove, slot, ridge or other desired structure can be formed in surface 42 in order to cooperate with corresponding structure formed on or in shell 12 to reduce or prevent rotation of liner 14 in shell 12.

Liner 14 includes a liner interface surface 44 which can, if desired, be shaped and finished to cooperate with locking ring 16 in order among other things to optimize polyethylene wear and/or constrain relative motion of liner 14 vis a vis locking ring 16 and/or shell 12.

Liner inner surface 30 is preferably hemispherical and finished as desired in order to optimize articulating and wear properties of inner bearing 34 relative to stem head 20. Inner surface 30 may feature a center of rotation which is different from the center of rotation of outer surface 26 of the shell and/or the first portion of shell cavity 38 or shell inner surface 40. Such geometry is sometimes referred to as "eccentric" and can be employed as desired and if desired in order to improve migration and/or other properties of prosthesis 10.

Locking ring 16 features an outer surface 48 which is adapted to correspond to and fit within shell cavity 38. It may be finished and shaped as desired, and it may include a non-rotational irregularity such as one or more irregularities 53 such as a tab, groove, slot, ridge or other structure which corresponds with one or more irregularities on shell inner surface 40 to reduce or prevent rotation of locking ring 16 relative to shell 12 and thus reduce polyethylene wear.

Outer surface 48 of locking ring 16 may include a groove or other structure 50 about all or a portion of the periphery of outer surface 48 for receiving retainer 18. A locking ring portal surface 52 together with portal surface 36 of shell 12 form the portal 54 or opening of prosthesis 10 through which head 20 and other portions of stem 24 extend. Some or all of portal surface 52 can include a surface of rotation or other modification 56 such as a chamfer or other non-curved or curved surface of rotation or a surface shaped as otherwise desired in order to improve clearance of stem 24 in portal 54 and thus increase range of motion of stem 24 relative to prosthesis 10. In the embodiment shown, FIGS. 1, 2, 6, 7 and 8, the surface 56 is a chamfer.

Locking ring portal surface 52 may transition through surface 56 or as otherwise desired to a capture surface 58 which forms the surface within prosthesis 10 of the least diameter about the center of rotation 46. Capture surface 58 of locking ring 16 may be, in cross-section, considered as cylindrical, rounded, or even a cusp. In any event, capture surface 58 of locking ring 16 which helps form the opening 54 in locking ring 16 and the prosthesis 10 is preferably substantially smaller in diameter about axis of rotation 46 than the largest diameter of stem head 20 about that axis (in all relevant desired orientations). As a result, when stem head 20 is captured within prosthesis 10, portions of locking ring 16 and in any event capture surface 58, form the mechanical structure which precludes or reduces dislocation of stem 24 from prosthesis 10.

Locking ring 16 also preferably includes an inner bearing surface 32 adapted to cooperate with head 20 in articulating relationship. Bearing surface 32 may be formed as surface of rotation with curvature corresponding generally to that of the stem head 20, and it may be surfaced as desired for optimal wear and mechanical properties.

The inner bearing surface 32 and its relationship to stem head 20 is important, because locking ring 16 and in particular inner bearing surface 32 absorb a substantial portion of tensile stress between stem 24 and prosthesis 20 such as that which would cause dislocation. Inner bearing surface 32 of locking ring 16 thus needs to be shaped and surfaced to reflect its reduced surface area which cooperates against stem head 20 in order to absorb the tensile load properly and optimally and to transfer it through locking ring 16 and retainer 18 to and through shell 12, without unnecessary motion between locking ring 16 and shell 12.

Figure 2:
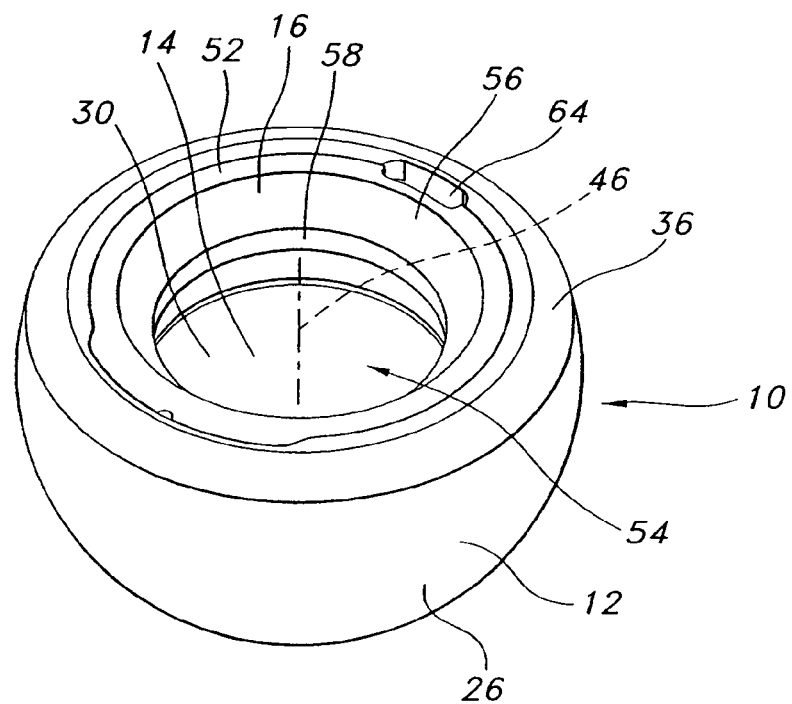
FIG. 2 is a perspective view of the prosthesis of FIG. 1.
Figure 3:
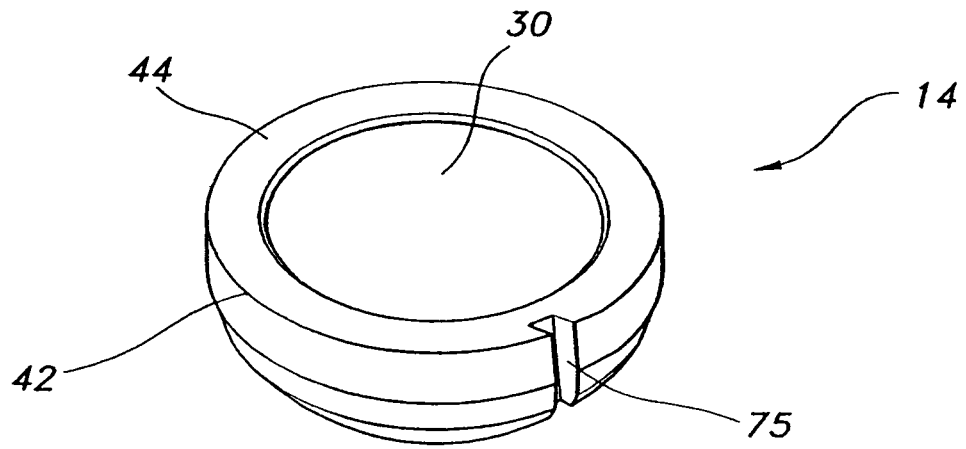
FIG. 3 is a perspective view of the liner of the prosthesis of FIG. 1.
Figure 4:
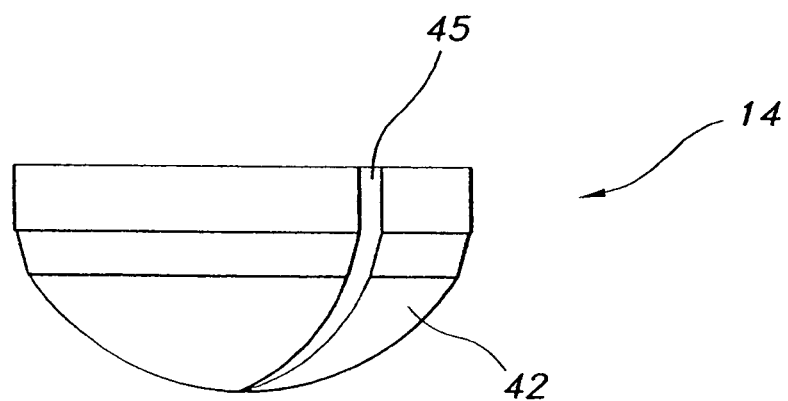
FIG. 4 is a side elevational view of the liner of FIG. 3.
Figure 5:
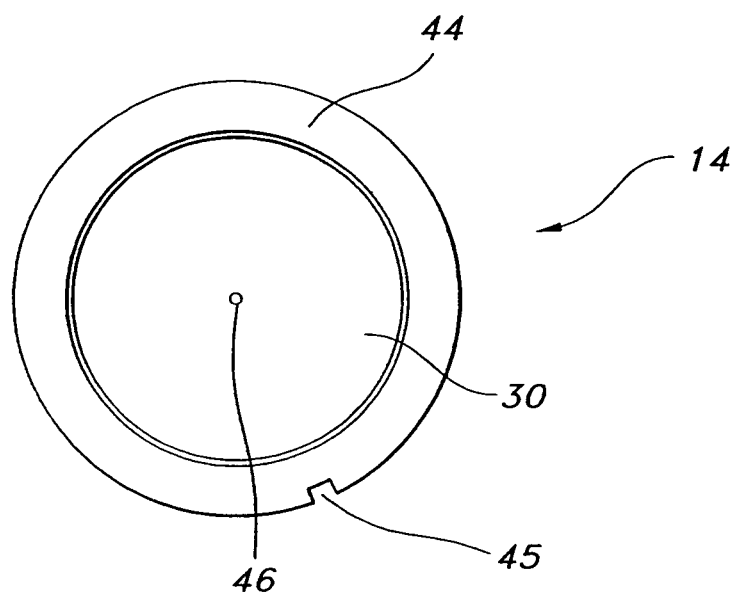
FIG. 5 is a plan view of the liner of FIG. 3.
Figure 6:
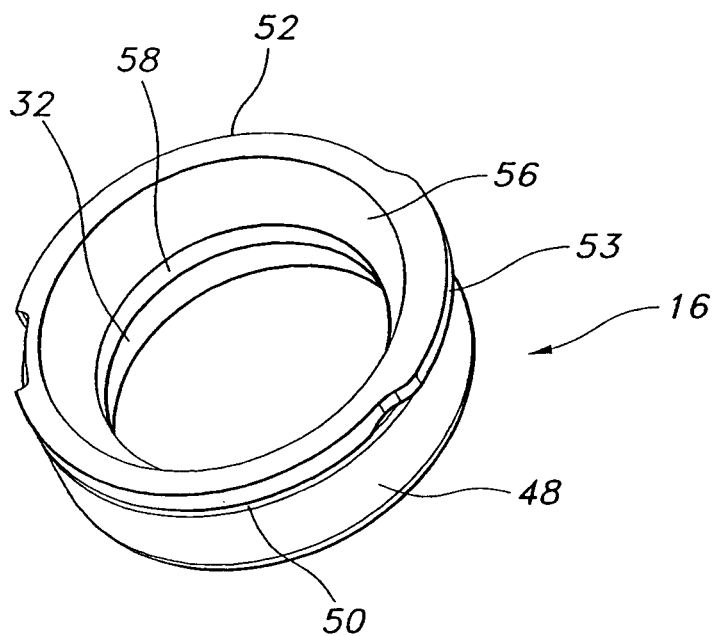
FIG. 6 is a perspective view of the locking ring of FIG. 1.
Figure 7:
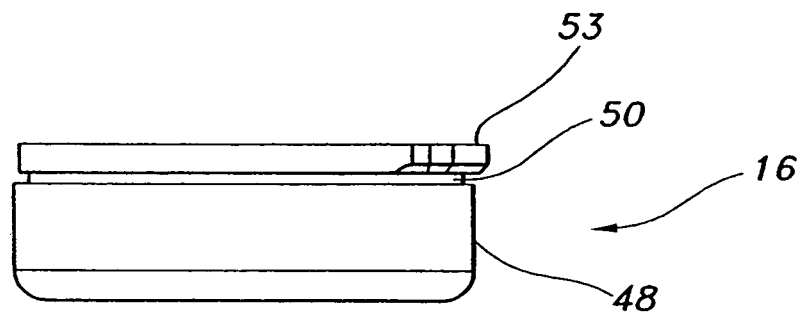
FIG. 7 is a side elevational view of the locking ring of FIG. 6.
Figure 8:
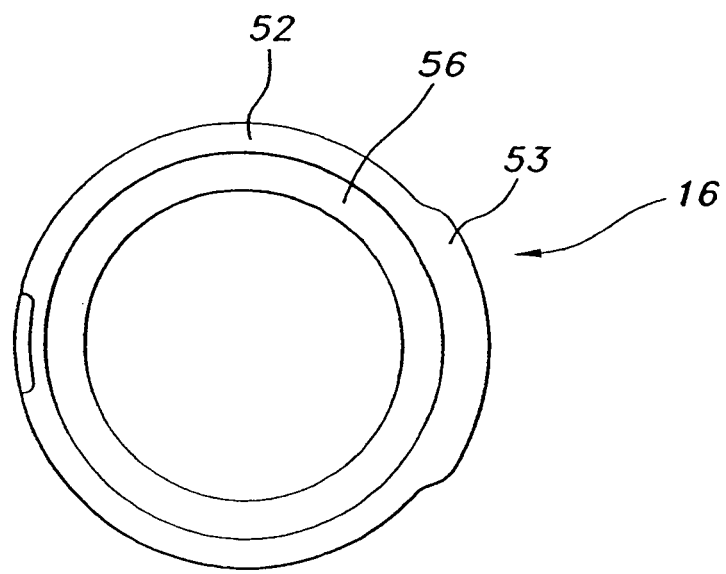
FIG. 8 is a plan view of the locking ring of FIG. 6.

Locking ring 16 is retained in and restrained in movement (at least in a direction parallel to axis of rotation 46) by retainer which fits within locking ring groove 50 and also a groove 62 formed in cavity 38 of shell 12. Retainer 18 may be formed of spring or other memory retaining metal and preferably fits closely to the shape of grooves 50 and 62, no matter what shape they may assume, to stabilize, restrain, and cause capture of locking ring 16 within shell 12 in an optimal fashion to, among other things, preclude pistoning of stem 24 and movement of liner 14. As shown in FIG. 2, an access 64 may be formed in shell portal surface 36 and/or liner portal surface 52 in order to access and manipulate retainer 18. In the preferred embodiment, retainer 18 may be a C-ring so that it can be compressed, and locking ring 16 and therefore stem 24 can be removed for disassembly or access.

Figure 9:
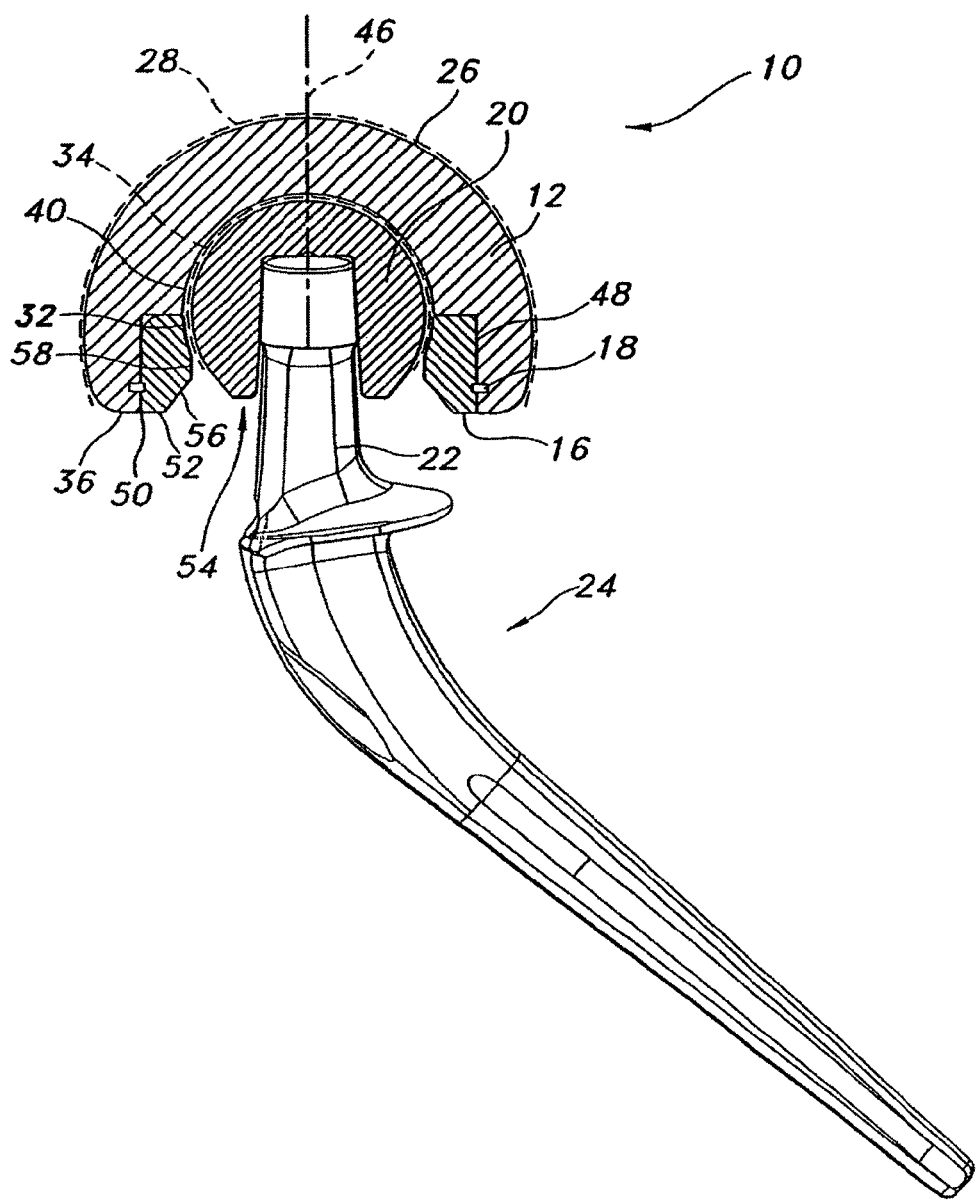
FIG. 9 is a schematic view of another embodiment of a prosthesis according to certain aspects of the present invention.

FIG. 9 shows a prosthesis 10 having a unitary design, without a liner. Here, head 20 of stem 24 fits directly within cavity 38 of shell 12 to form inner bearing 34. In this structure, head 20 may be of ceramic or metallic structure to cooperate with ceramic, metal, polyethylene shell 12 or shell 12 formed of another material. Configuration and operation of locking ring 16 and retainer 18 may be similar to that shown in FIG. 1. Locking ring 16 may be formed of ceramic, metal, polyethylene or any other desired material. Dislocation of stem 24 from prosthesis 10 is prevented or reduced by the reduced size of opening 24 by virtue of the non-split locking ring which is adapted to be assembled onto the neck 22 of the stem before the head 20 is mounted on the stem.

b. Treatment or Formation of Prosthetic Components to Improve, Accentuate or Optimize Properties Such as Material Wear or Resistance to Dislocation.

Treating or forming components or portions of them according to certain aspects of certain embodiments of the present invention in order to improve, accentuate or optimize properties such as, for instance, wear performance, and other components or portions of them in order to improve, accentuate or optimize other properties, such as, for instance, mechanical properties, is relevant to prosthetic implants in general, but particularly to hip prosthetic components including total hip replacement components, bipolar prosthetic components, unipolar components, and versions of any of these which include a shell, a combination of a shell and liner, a combination of a shell, liner and locking ring, or any other desired combination of components. Materials which can be the subject of such differential treatment or formation include not only polyethylene components, but also ceramic and metal components. The bipolar structure disclosed and shown in the drawings is therefore only a subset of the aspects of the invention having to do with such treatment or formation, and that disclosure and those drawings should not be interpreted or construed to read artificial structural limitations, such as limitations to a bipolar prosthetic component, into these aspects of the invention. However, it may be understood that the preferred embodiment of the invention relates to bipolar implants having a liner of polyethylene, part of all of which may be treated to improve bearing performance, e.g., by cross-linking.

As a first example of these aspects of the invention, consider any prosthesis which includes a polyethylene component. It is generally recognized that treating polyethylene such as ultra high molecular weight polyethylene in order to cross-link it, such as by irradiation before, during or after forming the article into shape, significantly and radically reduces polyethylene wear including polyethylene particle generation rates and volumetric wear rates. However, such treatment can also substantially alter mechanical properties of the polyethylene as shown in the following Table 1 which are results obtained from testing according to ASTM Standards D638 (yield strength, tensile strength and elongation testing) and ASTM F648 (impact strength testing) which are incorporated herein by this reference.

| | Mechanical Properties | | | |
|---|---|---|---|---|
| | Yield Strength (Mpa) | Tensile Strength (Mpa) | Elongation (%) | Impact Strength (kJ/m$^2$) |
| Non-XL | 22.2 | 48.2 | 390 | 96.1 |
| 5 Mrad | 20.4 | 42.1 | 289 | 82.16 |
| 10 Mrad | 21.0 | 37.1 | 237 | 69.4 |

According to this example, a total hip replacement acetabular component of conventional structure such as that shown in U.S. Pat. No. 5,310,408 entitled Acetabular Cup Body Prosthesis, Schryver et al. inventors, issued May 10, 1994, which is incorporated herein by this reference, can feature a polyethylene liner which is formed of differentially treated polyethylene according to these aspects of the invention. Thus, portions of the liner nearer the axis of rotation, and thus deeper within the component and thus which can be expected to bear a greater load from the femoral stem head, can be treated to improve, accentuate or optimize wear performance such as irradiation or other treatment to improve cross linking or wear performance. Portions nearer the lip which have more to do with retaining the femoral stem head in the liner and thus inhibiting dislocation of the head can feature reduced or no such treatment in order to improve, accentuate or optimize (here, retain) mechanical properties such as yield strength, tensile strength, elongation properties, and impact strength. In other words, two different types of polyethylene may be used to form the liner. For example, standard polyethylene may form one portion of the liner and cross-linked polyethylene may form another portion.

In other embodiments, more than two types of material may be used to form the liner. For example, the inner portion of the liner may be formed of ceramic (or any other suitable bearing material for joint articulation) and the outer portion may be polyethylene (or any other suitable bearing material for joint articulation), and some or all of the polyethylene material may be cross-linked. As a second example, in a bipolar prosthesis that features a shell, a liner and a locking ring, such as the embodiment shown in FIG. 1, polyethylene that improves, accentuates or optimizes wear properties such as polyethylene that has been irradiated or cross linked to a desired degree can be used in the liner 14 as opposed to the locking ring 16, which improves, accentuates or optimizes mechanical properties having to do with, for example, inhibiting dislocation of a femoral stem head. Alternatively, the nature and treatment of the polyethylene or other material may be varied in various portions of the liner 14, and various portions of the locking ring 16, and, for bipolar prostheses where no locking ring is used, in the liner 14. The bipolar prostheses suitable for such differential polyethylene treatment or formation need not include a locking ring, and if they do, that locking ring can be split or configured as desired. In such prostheses without a locking ring, the liner 14 is adapted for the stem head to be forced into the liner before or after the liner is inserted or placed into the shell. If provided, the locking ring may be formed of any appropriate material, including but not limited to poly-ether-ether-ketone (PEEK), poly-ether-ketone-ketone (PEKK), cross-linked polyethylene (XLPE), or standard polyethylene.

In alternative embodiments of bipolar prostheses according to this example which include liners and locking rings, various portions such as annular portions of the liner and locking ring may be treated as desired to improve, accentuate or optimize wear resistance and mechanical properties for optimal performance relative to the loads expected and received at those locations. For instance, concentric portions of the liner in the vicinity of axis of rotation may receive higher wear resistance treatment and portions toward the lip or opening of the liner may feature treatment or varying degrees of it which optimize the mechanical properties mentioned above in order, among other things, to reduce potential of femoral stem head dislocation. The treatment may be continuous from one location to the next, or it may be discontinuous. In bipolar structures in which no locking ring is employed, various portions of the liner may be treated as desired to optimize wear resistance on the one hand and the mechanical properties mentioned above on the other hand. Again, the treatment may vary from one location to the next in a continuous or discontinuous fashion or as otherwise desired.

In a narrower example, the inventors have found it advantageous in the preferred embodiment shown in FIG. 1 to form the locking ring 16 of generally non cross-linked ultra high molecular weight polyethylene while the liner 14 is formed of ultra high molecular weight polyethylene stock that has been treated using irradiation techniques to improve cross-linking. The shell and/or the femoral stem head can feature a surface that includes oxidized zirconium (as can components in any of the total hip replacement, bipolar, unipolar or other prostheses with which differential material treatment or formation according to these aspects of the invention are suitable.) Consequently, liner 14, which is generally absorbing the motion and wear from and imposed by head 20 of stem 24, is formed of the polyethylene that features better wear resistance. This improved wear resistance is significant, for the load imposed on liner 14 by head 20 can be three times body weight at a rate of one million or more cycles per year in the normal human. By contrast, the locking ring 16, which typically absorbs only loads caused by tendency of the stem 24 to withdraw through portal 54, can be made of polyethylene where wear resistance is perhaps less of an issue than the ability of the locking ring 16 to retain head 20 in the prosthesis 10 by virtue of higher yield strength, tensile strength, elongation, impact strength, and other mechanical properties having to do with robustness, reduced deformation, and as otherwise desired.

Various changes, modifications, additions, and/or deletions can be made to embodiments according to aspects of the present invention disclosed above without departing from this scope or spirit of the invention.

What is claimed is:

1. A hip prosthesis, comprising:
   a shell having an outer surface configured to engage acetabular tissue, the outer surface transitioning to a portal surface, and an inner surface forming a shell cavity;
   a liner disposed within the shell cavity;
   a non-split locking ring disposed within the shell, wherein in use a diameter of the locking ring is smaller than the largest diameter of a femoral head sized to articulate with the liner; and wherein the locking ring comprises a portal surface, at least a portion of which portal surface of the locking ring is coplanar with the portal surface of the shell; and
   a retainer for securing the locking ring and the shell, wherein the retainer is capturable in respective grooves formed in the shell and the locking ring, and wherein an access formed in the shell portal surface provides access to the retainer.

2. The hip prosthesis of claim 1, wherein the groove formed in the shell extends circumferentially about the inner surface of the shell.

3. The hip prosthesis of claim 2, wherein the groove formed in the locking ring extends circumferentially about the locking ring.

4. The hip prosthesis of claim 3, wherein the retainer is a C-ring.

5. The hip prosthesis of claim 1, further comprising an access formed in the locking ring portal surface that provides access to the retainer.

6. The hip prosthesis of claim 1, wherein the locking ring portal surface comprises a chamfer adapted to provide clearance for a femoral stem component in use.

7. A hip prosthesis comprising:
   a shell which includes an outer surface adapted to cooperate with acetabular tissue, the outer surface transitioning to a portal surface, and an inner surface forming a shell cavity;
   a liner adapted to fit within the shell cavity, the liner having an interface surface that does not extend to the portal surface of the shell; and an inner cavity having a diameter adapted to receive a femoral head component in use;
   a non-split locking ring adapted to cooperate with the shell to retain the femoral head component within the shell, the locking ring having an outer surface retained by a portion of the shell cavity, an upper portion facing the interface surface of the liner, and a portal surface opposite the upper portion, wherein at least a portion of the portal surface of the locking ring is coplanar with the portal surface of the shell; wherein the locking ring portal surface transitions to a capture surface on an inner portion of the locking ring that is smaller in diameter than the largest diameter of the femoral head component when in use, the capture surface adapted to bear against the femoral head component in articulating relationship in use in order to reduce dislocation of the femoral head component and a femoral stem in use; and
   a retainer adapted to be captured in the shell cavity in order to retain the locking ring in the shell, wherein an access formed in the shell portal surface provides access to the retainer.

8. The hip prosthesis according to claim 7 further comprising a femoral head component.

9. The hip prosthesis according to claim 8, wherein at least one of the shell and the femoral head component comprises a surface of oxidized zirconium.

10. The hip prosthesis according to claim 7 wherein the liner is adapted to articulate relative to the shell.

11. The hip prosthesis according to claim 7 wherein the liner is adapted to be locked into the shell.

12. The hip prosthesis according to claim 7 in which the locking ring defines a continuous, non-split annulus which forms an opening to receive the femoral stem, the opening having a diameter that is sufficiently small to mechanically prevent passage of said femoral head component through the locking ring.

13. The hip prosthesis according to claim 7, wherein the liner includes a first portion of treated polyethylene that provides improved polyethylene wear performance, and wherein the locking ring includes a portion of polyethylene that has not been treated, said portion of the locking ring having greater strength properties than said treated first portion of the liner.

14. The hip prosthesis of claim 13, wherein the liner further includes a second portion of polyethylene that remains untreated.

15. The hip prosthesis according to claim 7, wherein the liner is variably treated, such that at least one location on the inner cavity of the liner adapted to cooperate with the femoral head component is crosslinked to a greater degree than other locations of the liner.

16. The hip prosthesis according to claim 7, where the liner is variably crosslinked and the locking ring is not crosslinked.

17. The hip prosthesis of claim 7, wherein the liner comprises a multi-material liner comprising a first portion comprising polyethylene and a second portion comprising a material different than the first portion.

18. The hip prosthesis of claim 17, wherein the first portion comprises crosslinked polyethylene and the second portion comprises standard polyethylene.

19. The hip prosthesis of claim 17, wherein the first portion comprises cross-linked polyethylene and the second portion comprises ceramic.

20. The hip prosthesis according to claim 7, in which the shell cavity and the locking ring each contain a groove, wherein the retainer is configured to be captured in the grooves of the shell cavity and the locking ring in order to retain the locking ring in the shell.

21. The hip prosthesis according to claim 7, in which the shell cavity and the locking ring each include at least one irregularity, which irregularities are adapted to cooperate in order to reduce relative motion of the locking ring relative to the shell.

22. The hip prosthesis according to claim 7, in which the shell cavity and the liner each include at least one irregularity, which irregularities are adapted to cooperate in order to reduce relative motion of the liner relative to the shell.

23. The hip prosthesis of claim 7, wherein the locking ring portal surface comprises a chamfer adapted to provide clearance for the femoral stem in use.

24. The hip prosthesis of claim 7, wherein the non-split locking ring is resistant to deformation.

25. The hip prosthesis of claim 7, further comprising an access formed in the locking ring portal surface that provides access to the retainer.

\* \* \* \* \*